(12) United States Patent
Cotter et al.

(10) Patent No.: US 6,699,874 B2
(45) Date of Patent: Mar. 2, 2004

(54) FUNGICIDAL MIXTURES

(75) Inventors: Henry Van Tuyl Cotter, Trenton, NJ (US); Leslie May, Wokingham (GB); Gunter Reichert, Bubenheim (DE); Ewald Sieverding, St. Johann (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/314,594

(22) Filed: Dec. 10, 2002

(65) Prior Publication Data

US 2003/0206968 A1 Nov. 6, 2003

Related U.S. Application Data

(62) Division of application No. 09/809,512, filed on Mar. 15, 2001, now Pat. No. 6,518,275, which is a division of application No. 09/404,910, filed on Sep. 24, 1999, now Pat. No. 6,277,856.

(51) Int. Cl.$^7$ .................. A01N 43/54; A01N 37/12; A01N 43/46; C07D 487/04
(52) U.S. Cl. .................. 514/258; 544/263; 514/538; 514/539; 514/552; 514/217.06; 514/619; 514/210.21; 425/405
(58) Field of Search .................. 514/258, 210.21, 514/217.06, 539, 619; 544/263; 424/405

(56) References Cited

U.S. PATENT DOCUMENTS

| | | | |
|---|---|---|---|
| 5,593,996 A | 1/1997 | Pees et al. | 514/258 |
| 5,922,905 A | 7/1999 | Curtze et al. | 562/474 |
| 5,945,567 A | 8/1999 | Curtze et al. | 568/333 |
| 5,948,783 A | 9/1999 | Pees et al. | 514/258 |
| 6,346,535 B1 | 2/2002 | Cotter et al. | 514/269 |

FOREIGN PATENT DOCUMENTS

| | | |
|---|---|---|
| EP | 253213 | 3/1990 |
| EP | 550113 | 10/1997 |
| WO | 92/08703 | 5/1992 |

*Primary Examiner*—Sabiha Qazi
(74) *Attorney, Agent, or Firm*—Keil & Weinkauf

(57) ABSTRACT

Fungicidal compositions comprising an acceptable carrier and/or surface active agent and synergistically effective amounts of (a) at least one azolopyrimidine of formula I

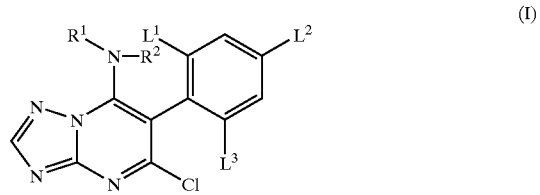

in which
$R^1$, $R^2$, $L^1$, $L^2$ and $L^3$ have the meaning given in claim 1; and (b) at least one fungicidal active ingredient selected from benomyl, carboxin, captan, chlorothalonil, copper oxychloride, cyprodinil, dimethomorph, dithianon, dodine, famoxadone, fenhexamid, fenpiclonil, fenpropimorph, fluazinam, mancozeb, metalaxyl, pyrimethanil, quinoxifen, sulfur, triforine, vinclozolin, a fungicidal triazole derivative, and a synthetic strobilurine derivative. The invention also provides a method of controlling the growth of phytopathogenic fungi at a locus by applying synergistically effective amounts of at least one azolopyrimidine of formula I and at least one fungicidal active ingredient (b) to the locus.

11 Claims, No Drawings

FUNGICIDAL MIXTURES

CROSS-REFERENCE TO RELATED APPLICATION(S)

This is a Divisional of application Ser. No. 09/809,512, filed Mar. 15, 2001, now U.S. Pat. No. 6,518,275 which is a dicisional of application Ser. No. 09/404,910, filed Sep. 24, 1999 (U.S. Pat. No. 6,277,856 B1), the entire disclosure of which is hereby incorporated by reference.

BACKGROUND OF THE INVENTION

The present invention relates to a fungicidal composition comprising a fungicidally acceptable carrier and/or surface active agent and synergistically effective amounts of
(a) at least one azolopyrimidine of formula I

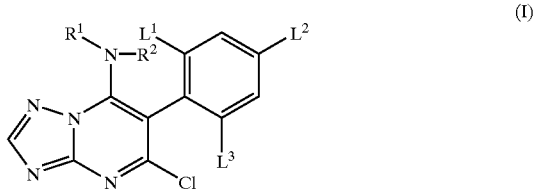

(I)

in which
$R^1$ represents a $C_{1-6}$ alkyl, $C_{3-6}$ alkenyl or $C_{1-6}$ haloalkyl group, or
$R^2$ represents a hydrogen atom or a $C_{1-6}$ alkyl group, or
$R^1$ and $R^2$ taken together represent a $C_{1-6}$ alkylene group,
$L^1$ represents a halogen atom;
$L^2$ and $L^3$ each independently represent a hydrogen or a halogen atom; and
and at least one fungicidal active ingredient selected from the following classes (A), (B) and (C):
  (A) a compound selected from the group consisting of benomyl, carboxin, captan, chlorothalonil, copper oxychloride, cyprodinil, dimethomorph, dithianon, dodine, famoxadone, fenpiclonil, fenpropimorph, fluazinam, mancozeb, metalaxyl, pyrimethanil, quinoxifen, sulfur, triforine and vinclozolin;
  (B) a fungicidal triazole derivative; and
  (C) a synthetic strobilurine derivative.

The fungicidal compounds of formula I to be used according to the present invention are known from U.S. patent U.S. Pat. No. 5,593,996. The compounds of the classes (A) and (B) are known from "The Pesticide Manual", 11$^{th}$ edition (1997), Editor Clive Tomlin. Fenhexamid is known from AGROW No. 287, p. 21. The synthetic strobilurines are known, for example, from WO 92/08703, EP 0 253 213 and EP 0 398 692.

However, none of the above mentioned prior art references teaches a combination of compounds of formula I with any of the fungicidal active ingredients selected from the classes (A), (B) and (C) as described above, nor that such mixtures show synergistic effects and can advantageously be used for controlling diseases such as wheat powdery mildew, barley powdery mildew, wheat leaf rust, barley net blotch and wheat Septoria leaf blotch, Botrytis diseases and others.

Surprisingly, when compounds of formula I were tank mixed with compounds from classes (A), (B) and (C) and used in greenhouse and field trials, a synergistic increases in activity were observed, compared to the activity expected based on the activities of the individual active ingredients.

A mixture of fungicides shows synergistic effect if the fungicidal activity of the mixture is larger than the sum of activities of the separately applied compounds. The expected fungicidal activity for a given mixture of two fungicides can also be calculated as follows (See Colby, S. R., "Calculating synergistic and antagonistic response of herbicide combinations", Weeds 15, pp 20–22 (1967):

$$EE=x+y-x \cdot y/100$$

wherein
x is the efficacy in % compared with an untreated control upon treatment with a fungicidal active ingredient A at a dose rate a;
y is the efficacy in % compared with an untreated control upon treatment with a fungicidal active ingredient B at a dose rate b;
EE is the expected efficacy with a combination of fungicidal active ingredients A and B at a dose of a+b, respectively.

If the actual efficacy (E) exceeds the expected (calculated) one (EE), the mixture displays a synergistic effect.

SUMMARY OF THE INVENTION

The present invention includes a fungicidal composition comprising an acceptable carrier and/or surface active agent and synergistically effective amounts of at least one compound of formula I, and at least one fungicidal active ingredient selected from the following classes (A), (B) and (C):
  (A) a compound selected from the group consisting of benomyl, carboxin, captan, chlorothalonil, copper oxychloride, cyprodinil, dimethomorph, dithianon, dodine, famoxadone, fenpiclonil, fenpropimorph, fluazinam, mancozeb, metalaxyl, pyrimethanil, quinoxifen, sulfur, triforine and vinclozolin;
  (B) a fungicidal triazole derivative; and
  (C) a synthetic strobilurine derivative.

The present invention also includes a method of controlling the growth of phytopathogenic fungi at a locus which comprises applying synergistically effective amounts of at least one azolopyrimidine of formula I and at least one fungicidally active ingredient selected from classes (A), (B) and (C) defined above to the locus.

DETAILED DESCRIPTION OF THE PREFERRED EMBODIMENTS

Preferred compounds of formula I are those wherein
$R^1$ and $R^2$ together with the interjacent nitrogen atom represent a 4-methylpiperidine ring, or wherein
$R^1$ represents a $C_{1-6}$ alkyl, in particular an isopropyl group, a $C_{1-6}$ haloalkyl, in particular a 2,2,2-trifluoroethyl or a 1,1,1-trifluoroprop-2-yl group, or a $C_{3-8}$ cycloalkyl group, in particular a cyclopentyl or cyclohexyl group and $R^2$ represents a hydrogen atom, and/or
wherein $L^1$ represents a fluorine or chlorine atom and $L^2$ and $L^3$ each independently represent a hydrogen atom or a fluorine atom, in particular
wherein $L^1$ represents fluorine, $L^2$ represents hydrogen and $L^3$ represents chlorine or wherein $L^1$ through $L^3$ represent fluorine.

Particularly preferred are the following azolopyrimidines: 5-chloro-6-(2-chloro-6-fluorophenyl)-7-(4-methylpiperid-1-yl)-[1,2,4]triazolo[1,5-a]pyrimidine coded Azoloyrimidine A, 5-chloro-6-(2-chloro-6-fluorophenyl)-7-(2,2,2-trifluoroethylamino)-[1,2,4]triazolo[1,5-a]pyrimidine coded Azoloyrimidine B and 5-chloro-6-(2,4,6-trifluorophenyl)-7-(1,1,1-trifluoroprop-2-ylamino)-[1,2,4]triazolo[1,5-a]pyrimidine coded Azoloyrimidine C. Azolopyrimidine C due to the chirality of its 1,1,1-trifluoroprop-2-yl group may be applied as a racemic mixture or in the form of an enantiomeric enriched compound, in particular as (S)-enantiomer coded (S)-Azolopyrimidine C.

Preferred triazole derivatives in the practice of this invention are the compounds of formula II,

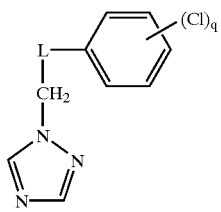
(II)

wherein

L represents a linking group selected from the groups (a), (b), (c) and (d)

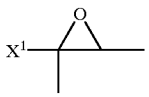
(a)

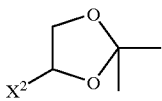
(b)

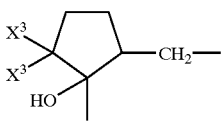
(c)

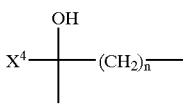
(d)

in which $X^1$ represents an alkyl or an optionally substituted phenyl group;

$X^2$ and $X^3$ each independently represent a hydrogen atom or an alkyl group;

$X^4$ represents an alkyl or cyclopropylalkyl group;

q is 1 or 2; and n is 0 or 2.

Particularly preferred are the triazoles selected from the group consisting of cyproconazole, epoxiconazole, metconazole, propiconazole and tebuconazole.

Preferred strobilurine derivatives in the practice of this invention are the compounds of formula III,

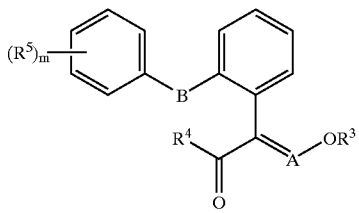
(III)

wherein

A represents N or CH;

B represents a —O—, —OCH$_2$—, a —CH$_2$O—, a pyrimid-4,6-dioxydiyl group or a group of formula

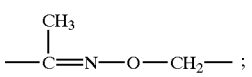

$R^3$ represents a $C_{1-4}$ alkyl group;

$R^4$ represents a $C_{1-6}$ alkoxy or a $C_{1-6}$ alkylamino group;

$R^5$ represents a hydrogen or halogen atom or a cyano, a $C_{1-4}$ alkyl or a $C_{1-4}$ haloalkyl group; and m is 0, 1 or 2;

in particular azoxystrobin, kresoxim methyl, CGA-279202 (AGROW 279, p.17 1998) or SSF126 (Pesticide Manual, loc. cit., page 1114)

Preferred compositions of this invention comprise the following constituents:

a carrier agent;

at least one azolopyrimidine of formula I, at least one compound selected from the classes (A), (B) and (C) as defined above;

optionally an adjuvant selected from the group consisting of polyalkoxylated alcohols, triglycerides and amines, in particular Synperonic 91–6, which is commercially available from ICI Surfactants;

optionally a foam breaking agent, in particular a mixture of perfluoroalkyphosphonic acids and/or perfluoroalkylphosphinic acids, in particular Defoamer SF or Fluowett PL, which are commercially available from Clariant GmbH.

The compound of formula I and the compound selected from the classes (A), (B) and (C) as defined above are to be applied together, in synergistically effective amounts. These synergistic mixtures exhibit an extraordinary efficacy against a broad range of phytopathogenic fungi, in particular against fungi from the classes ascomycetes, basidiomycetes, oomycetes and deuteromycetes. Therefore, they can be applied advantageously against a broad range of diseases in different crops. They may be applied as leaf, stem, root, into-water, seed dressing, nursery box or soil fungicides.

The composition according to the invention may be preferably applied for controlling phytopathogenic fungi of the genera: Achlya, Alternaria, Balansia, Bipolaris, Blumeria (Erysiphe), Cercospora, Cochliobolus, Curvularia, Cylindrocladium, Drechslera, Entyloma, Fusarium, Gaeumannomyces, Gerlachia, Gibberella, Guignardia, Leptosphaeria, Magnaporthe, Mucor, Mycosphaerella, Myrothecium, Nigrospora, Peronospora, Phoma, Pseudoperonospora, Pseudocercosporella, Phytophthora, Puccinia, Pyricularia, Pythium, Rhizoctonia, Rhizopus, Sarocladium, Sclerophthora, Sclerotium, Septoria, Tilletia, Uncinula, Ustilago, Ustilaginoidea, and Venturia, in particular the species *Blumeria graminis* f. sp. tritici, *Botrytis cinerea, Septoria tritici Erysiphe cichoracearum* and *Puccinia recondita*.

The compositions according to the invention are preferably applied for controlling the above phytopathogenic fungi on monocotyledoneous plants, such as barley and wheat, rice and turf grases, or fruit crops such as pomefruits, stonefruits and vines, as well as all kinds of vegetables, oil and oil seed crops, and ornamentals.

The application rate of the compound of formula I according to this invention is suitably in the range of 1 to 2000 grams of active ingredient (g a.i.) per hectare, with rates between 20–500 g a.i./ha often achieving satisfactory control. The optimal rate for a specific application will depend on the crop(s) under cultivation and the predominant species of infesting fungi, and readily may be determined by established biological tests known to those skilled in the art.

In general, the preferred application rate of the compounds of formula I is in the approximate range of 10 to 500 g a.i./ha, more preferably 20–300 g a.i./ha.

The optimal rate for the compounds of classes (A), (B) and (C), will, however, depend on the crop(s) under cultivation and the level of infestation by the fungus, and can readily be determined by established biological tests.

The approximate ratio (by weight) of the compound of formula I to the fungicidal active ingredient of the classes (A), (B) and (C) is suitably from 1:100 to 100:1. The preferred ratio formula I: (A), (B) or (C) may vary, e.g., from about 1:50 to about 50:1, in particular from about 1:4 to about 4:1, most preferably from 1:1.5 to 1.5:1.

The active compounds can be co-formulated together in a suitable ratio according to the present invention, together with carriers and/or additives known in the art.

A method of making such a composition is also provided which comprises bringing the compound of formula I and the fungicidal active ingredient selected from the classes (A), (B) and (C) as defined above into association with at least one carrier. It is also envisaged that different isomers or mixtures of isomers of formula I and/or the fungicidal active ingredient selected from the classes (A), (B) and (C) may have different levels or spectra of activity and thus compositions may comprise individual isomers or mixtures of isomers.

A composition according to the invention preferably contains from 0.1% to 99.9%, preferably 0.2 to 80% by weight (w/w) of active ingredients.

A carrier in a composition according to the invention may be any material with which the active ingredients may be formulated to facilitate application to the locus to be treated (which may, for example, be a plant, seed, foliage, soil, or into the water where the plant grow or to the roots), or to facilitate storage, transport or handling. A carrier may be a solid or a liquid, including material which is normally a gas but which has been compressed to form a liquid.

The compositions may be manufactured into, e.g., emulsion or emulsifiable concentrates, solutions, oil in water emulsions, wettable powders, soluble powders, suspension concentrates, dusts, granules, aerosols, water dispersible granules, tablets, micro-capsules, gels and other formulation types by well-established procedures. These procedures may include intensive mixing and/or milling of the active ingredients with other substances, such as fillers, solvents, solid carriers, surface active compounds (surfactants), and, optionally solid and/or liquid auxilaries and/or adjuvants. The form of application such as spraying, atomizing, dispersing or pouring may be chosen like the compositions according to the desired objectives and the given circumstances.

Solvents used in the composition of this invention may be aromatic hydrocarbons, e.g. Solvesso® 200, substituted naphthalenes, phthalic acid esters, such as dibutyl or dioctyl phthalate, aliphatic hydrocarbons, e.g. cyclohexane or paraffins, alcohols and glycols as well as their ethers and esters, e.g. ethanol, ethyleneglycol mono- and dimethyl ether, ketones such as cyclohexanone, strongly polar solvents such as N-methyl-2-pyrrolidone, or γ-butyrolactone, higher alkyl pyrrolidones, e.g. n-octylpyrrolidone or cyclohexylpyrrolidone, epoxidized plant oil esters, e.g. methylated coconut or soybean oil ester and water. Mixtures of different solvents may be suitable.

Solid carriers used in the composition of this invention which may be used for dusts, wettable powders, water dispersible granules, or granules, may be mineral fillers, such as calcite, talc, kaolin, montmorillonite or attapulgite or others. The physical properties may be improved by addition of highly dispersed silica gel or polymers. Carriers for granules may be porous material, e.g., pumice, kaolin, sepiolite, bentonite; non-sorptive carriers may be calcite or sand or others. Additionally, a multitude of pre-granulated inorganic or organic materials may be used, such as dolomite or crushed plant residues.

Pesticidal compositions are often formulated and transported in a concentrated form which is subsequently diluted by the user before application. The presence of small amounts of a carrier which is a surfactant facilitates this process of dilution. Thus, preferably at least one carrier in a composition according to the invention is a surfactant. For example, the composition may contain two or more carriers, at least one of which is a surfactant.

Surfactants may be nonionic, anionic, cationic or zwitterionic substances with good dispersing, emulsifying and wetting properties, depending on the nature of the active ingredients to be formulated. Surfactants may also include mixtures of individual surfactants.

Wettable powders in this invention suitably may contain about 5 to 90% w/w of active ingredient and, in addition to solid inert carrier, about 3 to 10% w/w of dispersing and wetting agents and, where necessary, 0 to 10% w/w of stabilizer(s) and/or other additives such as penetrants or stickers. Dusts may be formulated as a dust concentrate having a similar composition to that of a wettable powder but without a dispersant, and may be diluted in the field with further solid carrier to give a composition containing about 0.5 to 10% w/w of active ingredient. Water dispersible granules and granules may have a size approximately between 0.15 mm and 2.0 mm, and may be manufactured by a variety of techniques known in the art. These granules suitably will contain about 0.5 to 90% w/w active ingredient and 0 to 20% w/w of additives such as stabilizer, surfactants, slow release modifiers and binding agents. Emulsifiable concentrates suitably may contain, in addition to a solvent or a mixture of solvents, approximately 1 to 80% w/v active ingredient, 2 to 20% w/v emulsifiers and 0 to 20% w/v of other additives, such as stabilizers, penetrants and corrosion inhibitors. Suspension concentrates may be milled so as to obtain a stable, non-sedimenting flowable product and suitably contain about 5 to 75% w/v active ingredient, and 0.5 to 15% w/v of dispersing agents, 0.1 to 10% w/v of suspending agents such as protective colloids and thixotropic agents, 0 to 10% w/v of other additives such as defoamers, corrosion inhibitors, stabilizers, penetrants and stickers, and water or an organic liquid in which the active ingredient is substantially insoluble; certain organic solids or inorganic salts may be present dissolved in the formulation to assist in preventing sedimentation and crystalization or as antifreeze agents.

Aqueous dispersions and emulsions, for example compositions obtained by diluting the formulated product according to the invention with water, also lie within the scope of the invention.

The invention also encompasses the use of a carrier which will provide slow release of the pesticidal compounds into the environment of a plant which is to be protected, to extend the duration of the protective activity of the composition.

The biological activity of the active ingredients may be increased by including an adjuvant in the formulation or a spray dilution. An adjuvant is defined here as a substance which can increase the biological activity of an active ingredient but is not itself significantly biologically active. The adjuvant can either be included in the formulation as a coformulant or carrier, or can be added to the spray tank together with the formulation containing the active ingredient.

As a commodity, the compositions may preferably be in a concentrated form whereas the end user generally employs diluted compositions. The compositions may be diluted to a concentration down to about 0.001% of active ingredient. The doses preferably are in the approximate range from 0.01 to 10 kg a.i./ha.

Examples of formulations useful in the practice of the invention are:

SC-I 1

| | | |
|---|---|---|
| active ingredient | Azolopyrimidine C | 100.0 g |
| Dispersing agent | Morwet D425[1] | 25.0 g |
| Dispersing agent | Pluronic ® PE 10500[2] | 5.0 g |
| Antifoaming agent | Rhodorsil ® 426R[3] | 1.5 g |
| Dispersing agent | Rhodopol ® 23[3] | 2.0 g |
| Antifreezing agent | Propylene glycol | 80.0 g |
| Biocidal agent | Proxel ® GXL[4] | 1.0 g |
| Water | | to 1000 ml |

SC-I 2

| | | |
|---|---|---|
| active ingredient | Azolopyrimidine C | 100.0 g |
| Dispersing agent | Soprophor ® FL[3] | 30.0 g |
| Antifoaming agent | Rhodorsil ® 426R[3] | 1.5 g |
| Dispersing agent | Rhodopol ® 23[3] | 2.0 g |
| Antifreezing agent | Propylene glycol | 80.0 g |
| Biocidal agent | Proxe l ® GXL[4] | 1.0 g |
| Water | | to 1000 ml |

SC-A/B/C

| | | |
|---|---|---|
| active ingredient | selected from classes (A), (B), (C) | 200.0 g |
| Dispersing agent | Soprophor ® FL[3] | 25.0 g |
| Antifoaming agent | Rhodorsil ® 426R[3] | 1.5 g |
| Dispersing agent | Rhodopol ® 23[3] | 2.0 g |
| Antifreezing agent | Propylene glycol | 80.0 g |
| Biocidal agent | Proxel ® GXL[4] | 1.0 g |
| Water | | to 1000 ml |

SC-I + A/B/C

| | | |
|---|---|---|
| active ingredient | Azolopyrimidine C | 60.0 g |
| active ingredient | selected from classes (A), (B) and (C) | 120.0 g |
| Dispersing agent | Soprophor ® FL[3] | 25.0 g |
| Antifoaming agent | Rhodorsil ® 426R[3] | 1.5 g |
| Dispersing agent | Rhodopol ® 23[3] | 2.0 g |
| Antifreezing agent | Propylene glycol | 80.0 g |
| Biocidal agent | Proxel ® GXL [4] | 1.0 g |
| Water | | to 1000 ml |

DC-I 1

| | | |
|---|---|---|
| active ingredient | Azolopyrimidine A | 100.0 g |
| Wetting agent | Pluronic ® PE6400[2] | 50.0 g |
| Dispersing agent | Lutensol ® TO 12[2] | 50.0 g |
| Solvent | benzyl alcohol | to 1000 ml |

[1]Product commercially available from Witco
[2]Product commercially available from BASF AG, Germany
[3]Product commercially available from Rhone-Poulenc
[4]Product commercially available from Zeneca The formulation SC-A/B/C, comprising a compound selected from the classes (A), (B) and (C), may be mixed with any of the other formulations SC-I 1, SC-I 2, SC-I 3, or DC-I which comprise the Azolopyrimidine C to produce a composition of this invention.

In a preferred embodiment of the invention, each active ingredient is added to a tank mix in a separate formulation, to form a composition of this invention.

The present invention also relates to a kit for the preparation of a spray mixture consisting of two separate units:

(i) a unit which comprises at least one azolopyrimidine of formula I, in particular one or more compounds selected from the Azolopyrimidines A, B or C, conventional carriers and optionally adjuvants;

(ii) a unit which comprises at least one active ingredient selected from the classes (A), (B) and (C), preferably one or more compounds selected from the group consisting of carboxin, fluazinam, quinoxifen, metalaxyl, famoxadone, metconazole, epoxiconazole, propiconazole, azoxystrobin or kresoxim methyl conventional carriers and optionally adjuvants.

In a preferred embodiment, the kit includes two bottles with dispensing means which allow the easy and correct addition of the active ingredients to the tank mix.

A composition according to the invention preferably contains from about 0.5% to 95% by weight of active ingredients.

The compositions of this invention may be diluted down to a concentration of about 0.0001% of active ingredients.

The compositions of this invention can be applied to the plants or their environment simultaneously with or in succession with other active substances. These other active substances can be either fertilizers, agents which donate trace elements, or other preparations which influence plant growth. However, they can also be other fungicides, selective herbicides, insecticides, bactericides, nematicides, algicides, molluscidides, rodenticides, virucides, compounds inducing resistance into plants, biological control agents such as viruses, bacteria, nematodes, fungi and other microorganisms, repellents of birds and animals, and plant growth regulators, or mixtures of several of these preparations, if appropriate together with other carrier substances conventionally used in the art of formulation, surfactants or other additives which promote application.

Examples of insecticidal compounds useful in this invention are alpha-cypermethrin, benfuracarb, BPMC, buprofezine, carbosulfan, cartap, chlorfenvinphos, chlorpyrifos-methyl, cycloprothrin, cypermethrin, esfenvalerate, ethofenprox, fenpropathrin, flucythrinate, flufenoxuron, hydramethylnon, imidacloprid, isoxathion, MEP, MPP, nitenpyram, PAP, permethrin, propaphos, pymetrozine, silafluofen, tebufenozide, teflubenzuron, temephos, terbufos, tetrachlorvinphos and triazamate.

Examples of biological control agents useful in this invention are: *Bacillus thuringiensis, Verticillium lecanii, Autographica californica* NPV, *Beauvaria bassiana, Ampelomyces quisqualis, Bacilis subtilis, Pseudomonas fluorescens, Steptomyces griseoviridis* and *Trichoderma harzianum*.

Examples of chemical agents that induce systemic acquired resistance in plants are: isonicotinic acid or derivatives thereof, 2,2-dichloro-3,3-dimethylcyclopropylcarboxylic acid and BION.

The present invention is of wide applicability in the protection of crops, trees, residential and ornamental plants against fungal attack. Preferred crops are cereals, such as wheat and barley, rice, vines, and apples. The duration of the protection is normally dependent on the individual compound selected, and also a variety of external factors, such as climate, the impact of which may be mitigated by the use of a suitable formulation.

The following examples further illustrate the present invention. It should be understood, however, that the invention is not limited solely to the particular examples given below.

EXAMPLES

General Methods

The trials are carried out under greenhouse (Examples 1 to 32) or field conditions (Examples 33 to 40) in residual or curative applications. The fungicides are applied in single treatments, or in a combination comprising an azolopyrimidine of formula I and a compound selected from the classes (A), (B) and (C) as defined above. The compounds are applied in form of an aqueous spray mix obtained from a concentrated formulation or the technical material.

I. Cereals and Dicots—Greenhouse

1. Seed is planted in 6 cm diameter plastic pots and maintained in the greenhouse.
2. When the primary leaf is fully expanded in the case of cereals or several leaves are present in the case of dicots, formulated test compounds are sprayed with a three nozzle overhead fungicide sprayer to near run-off. Alternatively, a single nozzle overhead track sprayer is used for application of the compounds to cereals at a rate of 200 l/ha. Plants are then allowed to air-dry.
3. Inoculation precedes treatment in the case of curative evaluations and follows treatment in case of residual evaluations. For inoculation of powdery mildew disease, plants are set up on greenhouse benches with bottom watering mats and inoculated by dusting them with conidia from infected plants. Between inoculation and treatment for curative evaluations and between treatment and inoculation for residual evaluations, plants are maintained in the greenhouse with bottom watering.

For inoculation of non-powdery mildew diseases, an aqueous spore suspension of the pathogen is applied to the plant and the plants are kept 1–2 days in a moist infection chamber before being returned to the greenhouse where they are maintained by bottom watering.

4. Disease on the foliage as percent leaf area with disease symptoms/signs is evaluated about 7 days after inoculation. In the case of wheat, the tips and bases of the leaves are excluded from the evaluation.

$$\% \text{ disease control} = 100 - \frac{\% \text{ disease in treated plants}}{\% \text{ disease in untreated plants}} \times 100\%$$

FORMULATION, REFERENCE COMPOUNDS AND CONTROLS

1. Technical compounds are formulated in a solvent/surfactant system consisting of 5% acetone and 0.05% Tween 20 in deionized water. Compounds are dissolved in acetone prior to addition of the water; the Tween 20 can be added through either the acetone or the water. Dilutions are made using the solvent/surfactant system. Formulated compounds are prepared using deionized water.
2. Two kinds of controls are included:
   Plants treated with the solvent/surfactant solution and inoculated (Solvent Blank).
   Untreated plants which are inoculated (Inoculated Control).

For the field study formulated Azolopyrimidine A, B or C and formulated compounds from the classes (A), (B) and (C) were used.

Evaluation of the Disease

Assessments of the diseases took place at the indicated day after the application of the compounds. Per cent infected leaf area infected was evaluated. The efficacy of the compounds/compounds mixtures to control the diseases was calculated by using the formula given above under item 4:

II. Apple Fruit Botrytis

1. Apples (Malus X domestica Borkh.) variety Golden Delicious are disinfected by washing them briefly in 70% ethanol. After drying the apples are marked with four short equal-distant lines indicating the positions to be wounded.
2. Corresponding with the marks, four holes are poked around the apple equator with a pipette tip. 10 µl of the treatment solution are pipetted into each hole.
3. Three hours after application, 10 µl of a conidial suspension of Botrytis cinerea are pipetted into each. For incubation, the treated/inoculated apples are set up for five days.
4. Disease occurs as rotten apple tissue surrounding the inoculated wounds. The diameter of the rotten zone around each wound is measured.

FORMULATION, REFERENCE COMPOUNDS AND CONTROLS

1. Technical compounds are formulated in a solvent system consisting of 5% acetone and 0.05% Tween 20 in deionized water. Compounds are dissolved in acetone prior to dilution with water. Formulated compounds are prepared using deionized water.
2. Three kinds of controls are included:
   Apples treated with the solvent solution and inoculated (Solvent Blank).
   Untreated apples which are inoculated (Inoculated Control).
   Untreated apples which are not inoculated (Uninoculated Control).

Evaluation of the Disease

Assessments of the diseases took place at the indicated day after the application of the compounds. Per cent infected leaf area infected was evaluated. The efficacy of the compounds/compounds mixtures to control the diseases was calculated by using the formula:

$$\% \text{ disease control} = 100 - \frac{\text{mean of diameters on treated apples}}{\text{mean of diameters on untreated apples}} \times 100\%$$

Determination of Synergy

Synergy was calculated using the % disease control values of specific treatments for the two COLBY formula given hereinabove III. Field Tests The compounds are applied according to good agricultural practice in the form of an aqueous spray mix obtained from a concentrated formulation or the technical material at a rate of 400 l/ha. The disease control is evaluated according to the formula given for the greenhouse tests.

A Greenhouse Tests

Example 1

Fungicidal efficacy of the mixture of Azolopyrimidine A+fenpropimorph (3 day residual) against *Leptosphaeria nodorum* on wheat.

The tank mix was obtained from technical material of Azolopyrimidine A and an EC formulation containing 750 g fenpropimorph per liter. The observed and expected efficacies with different rates are given in Table I:

TABLE I

| dose rate (ppm) | | Observed | Expected |
|---|---|---|---|
| Azolopyrimidine A | fenpropimorph | Efficacy | Efficacy |
| 100 | 0 | 40 | — |
| 10 | 0 | 35 | — |
| 0 | 5 | 15 | — |
| 0 | 0.5 | 19 | — |
| 100 | 5 | 71 | 49 |
| 100 | 0.5 | 80 | 51 |
| 10 | 5 | 55 | 45 |
| 10 | 0.5 | 50 | 47 |

Example 2

Fungicidal efficacy of the mixture of Azolopyrimidine A+tebuconazole (3 day residual) against *Leptosphaeria nodorum* on wheat.

The tank mix was obtained from technical material of Azolopyrimidine A and an EC formulation containing 250 g tebuconazole per liter. The observed and expected efficacies with different rates are given in Table II:

TABLE II

| dose rate (ppm) | | Observed | Expected |
|---|---|---|---|
| Azolopyrimidine A | tebuconazole | Efficacy | Efficacy |
| 100 | 0 | 40 | — |
| 0 | 0.2 | 19 | — |
| 0 | 0.02 | 25 | — |
| 100 | 0.2 | 88 | 51 |
| 100 | 0.02 | 87 | 55 |

Example 3

Fungicidal efficacy of the mixture of Azolopyrimidine A+tebuconazole (2 day residual) against *Blumeria graminis* on wheat.

The tank mix was obtained from technical material of Azolopyrimidine A and an EC formulation containing 250 g tebuconazole per liter. The observed expected efficacies with different rates are given in Table III:

TABLE III

| dose rate (ppm) | | Observed | Expected |
|---|---|---|---|
| Azolopyrimidine A | tebuconazole | Efficacy | Efficacy |
| 10 | 0 | 14 | — |
| 0 | 0.2 | 9 | — |
| 0 | 0.02 | 2 | — |
| 10 | 0.2 | 52 | 22 |
| 10 | 0.02 | 33 | 16 |

Example 4

Fungicidal efficacy of the mixture of Azolopyrimidine A+vinclozolin (3 day residual) against *Botrytis cinerea* on apple fruits.

The tank mix was obtained from technical material of Azolopyrimidine A and a WG formulation containing 500 g vinclozolin per kg. The observed and expected efficacies with different rates are given in Table IV:

TABLE IV

| dose rate (ppm) | | Observed | Expected |
|---|---|---|---|
| Azolopyrimidine A | vinclozolin | Efficacy | Efficacy |
| 10 | 0 | 33 | — |
| 1 | 0 | 0 | — |
| 0 | 10 | 8 | — |
| 10 | 10 | 54 | 38 |
| 1 | 10 | 31 | 8 |

Example 5

Fungicidal efficacy of the mixture of Azolopyrimidine A+cyprodinil (3 day residual) against *Botrytis cinerea* on apple fruits.

The tank mix was obtained from technical material of Azolopyrimidine A and a WG formulation containing 750 g cyprodinil per kg. The observed and expected efficacies with different rates are given in Table V:

TABLE V

| dose rate (ppm) | | Observed | Expected |
|---|---|---|---|
| Azolopyrimidine A | cyprodinil | Efficacy | Efficacy |
| 10 | 0 | 33 | — |
| 1 | 0 | 0 | — |
| 0 | 1 | 46 | — |
| 0 | 0.1 | 2 | — |
| 10 | 1 | 66 | 64 |
| 10 | 0.1 | 61 | 34 |
| 1 | 0.1 | 3 | 2 |

Example 6

Fungicidal efficacy of the mixture of Azolopyrimidine A+benomyl (3 day residual) against *Botrytis cinerea* on apple fruits.

The tank mix was obtained from technical material of Azolopyrimidine A and a WP formulation containing 500 g benomyl per kg. The observed and expected efficacies with different rates are given in Table VI:

TABLE VI

| dose rate (ppm) | | Observed | Expected |
|---|---|---|---|
| Azolopyrimidine A | benomyl | Efficacy | Efficacy |
| 10 | 0 | 25 | — |
| 1 | 0 | 0 | — |
| 0 | 10 | 13 | — |
| 0 | 1 | 0 | — |
| 10 | 10 | 87 | 35 |
| 10 | 1 | 38 | 25 |
| 1 | 10 | 35 | 13 |
| 1 | 1 | 15 | 0 |

Example 7

Fungicidal efficacy of the mixture of Azolopyrimidine A+vinclozolin (3 day residual) against *Botrytis cinerea* on apple fruits.

The tank mix was obtained from technical material of Azolopyrimidine A and a WG formulation containing 500 g vinclozolin per kg. The observed and expected efficacies with different rates are given in Table VII:

TABLE VII

| dose rate (ppm) | | Observed | Expected |
|---|---|---|---|
| Azolopyrimidine A | Vinclozolin | Efficacy | Efficacy |
| 10 | 0 | 25 | — |
| 1 | 0 | 0 | — |
| 0 | 10 | 17 | — |
| 0 | 1 | 0 | — |
| 10 | 10 | 57 | 38 |
| 1 | 1 | 4 | 0 |

Example 8

Fungicidal efficacy of the mixture of Azolopyrimidine C+metconazole (1 day residual) against *Rhynchosporium secalis* on barley.

The tank mix was obtained from technical materials of Azolopyrimidine C and metconazole. The observed and expected efficacies are given in Table VIII:

TABLE VIII

| dose rate (ppm) | | Observed | Expected |
|---|---|---|---|
| Azolopyrimidine C | metconazole | Efficacy | Efficacy |
| 100 | 0 | 15 | — |
| 0 | 100 | 87 | — |
| 100 | 100 | 100 | 89 |

Example 9

Fungicidal efficacy of the mixture of Azolopyrimidine C+metconazole (1 day residual) against *Septoria tritici* on wheat.

The tank mix was obtained from a SC formulation containing 100 g Azoplopyrimidine C per liter and an EC containing 100 g metconazole per liter. The observed and expected efficacies with different rates are given in Table IX:

TABLE IX

| dose rate (ppm) | | Observed | Expected |
|---|---|---|---|
| Azolopyrimidine C | metconazole | Efficacy | Efficacy |
| 40 | 0 | 91 | — |
| 25 | 0 | 68 | — |
| 8 | 0 | 0 | — |
| 5 | 0 | 0 | — |
| 2 | 0 | 0 | — |
| 0 | 25 | 0 | — |
| 0 | 10 | 0 | — |
| 0 | 8 | 0 | — |
| 0 | 5 | 0 | — |
| 0 | 2 | 0 | — |
| 40 | 10 | 92 | 91 |
| 25 | 25 | 89 | 68 |
| 8 | 2 | 11 | 0 |
| 5 | 5 | 16 | 0 |
| 2 | 8 | 28 | 0 |

Example 10

Fungicidal efficacy of the mixture of Azolopyrimidine C+metconazole (1 day residual) against *Pyrenophora teres* on barley.

The tank mix was obtained from a SC formulation containing 100 g Azolopyrimidine C per liter and an EC containing 100 g metconazole per liter. The observed and expected efficacies with different rates are given in Table X:

TABLE X

| dose rate (ppm) | | Observed | Expected |
|---|---|---|---|
| Azolopyrimidine C | Metconazole | Efficacy | Efficacy |
| 125 | 0 | 0 | — |
| 50 | 0 | 0 | — |
| 40 | 0 | 0 | — |
| 25 | 0 | 0 | — |
| 10 | 0 | 0 | — |
| 0 | 200 | 73 | — |
| 0 | 125 | 68 | — |
| 0 | 40 | 34 | — |
| 0 | 25 | 9 | — |
| 0 | 10 | 4 | — |
| 125 | 125 | 69 | 68 |
| 50 | 200 | 82 | 73 |
| 25 | 25 | 46 | 9 |
| 40 | 10 | 9 | 4 |
| 10 | 40 | 51 | 34 |

Example 11

Fungicidal efficacy of the mixture of Azolopyrimidine C+metconazole (1 day residual) against *Puccinia recondita* on wheat.

The tank mix was obtained from from a SC formulation containing 100 g Azolopyrimidine C per liter and an EC containing 100 g metconazole per liter. The observed and expected efficacies with different rates are given in Table XI:

TABLE XI

| dose rate (ppm) | | Observed | Expected |
|---|---|---|---|
| Azolopyrimidine C | metconazole | Efficacy | Efficacy |
| 200 | 0 | 35 | — |
| 125 | 0 | 20 | — |
| 40 | 0 | 10 | — |
| 25 | 0 | 5 | — |
| 10 | 0 | 3 | — |
| 8 | 0 | 1 | — |
| 2 | 0 | 2 | — |
| 0 | 125 | 97 | — |
| 0 | 50 | 72 | — |
| 0 | 40 | 31 | — |
| 0 | 25 | 14 | — |
| 0 | 10 | 8 | — |
| 0 | 8 | 0 | — |
| 0 | 2 | 0 | — |
| 200 | 50 | 86 | 82 |
| 125 | 125 | 99 | 98 |
| 40 | 10 | 25 | 17 |
| 25 | 25 | 22 | 18 |
| 10 | 40 | 70 | 33 |
| 8 | 2 | 1 | 1 |
| 2 | 8 | 8 | 2 |

Example 12

Fungicidal efficacy of the mixture of Azolopyrimidine C+kresoxim methyl (1 day curative) against *Puccinia recondita* on wheat.

Plants sprayed twice, once with each compound. The tank mixes were obtained from a SC formulation containing 100 g Azolopyrimidine C per liter and a WG containing 500 g kresoxim methyl per kg. The observed and expected efficacies with different rates are given in Table XII:

TABLE XII

| dose rate (ppm) | | Observed | Expected |
|---|---|---|---|
| (S)-Azolopyrimidine C | kresoxim methyl | Efficacy | Efficacy |
| 400 | 0 | 99 | — |
| 200 | 0 | 97 | — |
| 100 | 0 | 79 | — |
| 50 | 0 | 66 | — |
| 25 | 0 | 25 | — |
| 0 | 400 | 5 | — |
| 0 | 200 | 1 | — |
| 0 | 100 | 0 | — |
| 0 | 50 | 1 | — |
| 0 | 25 | 0 | — |
| 400 | 400 | 99 | 99 |
| 200 | 200 | 94 | 97 |
| 100 | 100 | 86 | 79 |
| 50 | 50 | 84 | 66 |
| 25 | 25 | 29 | 25 |

Example 13

Fungicidal efficacy of the mixture of Azolopyrimidine C+carboxin (1 day residual) against *Puccinia recondita* on wheat.

The tank mix was obtained from technical material of Azolopyrimidine C and WP formulation containing 750 g carboxin per kg. The observed and expected efficacies with different rates are given in Table XIII:

TABLE XIII

| dose rate (ppm) | | Observed | Expected |
|---|---|---|---|
| Azolopyrimidine C | carboxin | Efficacy | Efficacy |
| 4 | 0 | 100 | — |
| 1 | 0 | 71 | — |
| 0.25 | 0 | 41 | — |
| 0.06 | 0 | 8 | — |
| 0 | 4 | 4 | — |
| 0 | 1 | 0 | — |
| 0 | 0.25 | 0 | — |
| 0 | 0.06 | 0 | — |
| 4 | 4 | 100 | 100 |
| 1 | 1 | 89 | 71 |
| 0.25 | 0.25 | 66 | 49 |
| 0.06 | 0.06 | 59 | 8 |

Example 14

Fungicidal efficacy of the mixture of Azolopyrimidine C+fluazinam (1 day residual) against *Puccinia recondita* on wheat.

The tank mix was obtained from technical material of Azolopyrimidine C and a SC formulation containing 500 g fluazinam per liter. The observed and expected efficacies with different rates are given in Table XIV:

TABLE XIV

| dose rate (ppm) | | Observed | Expected |
|---|---|---|---|
| Azolopyrimidine C | fluazinam | Efficacy | Efficacy |
| 4 | 0 | 100 | — |
| 1 | 0 | 71 | — |
| 0.06 | 0 | 8 | — |
| 0 | 4 | 17 | — |
| 0 | 1 | 4 | — |
| 0 | 0.06 | 0 | — |
| 4 | 4 | 100 | 100 |
| 1 | 1 | 92 | 72 |
| 0.06 | 0.06 | 24 | 8 |

Example 15

Fungicidal efficacy of the mixture of Azolopyrimidine C+quinoxyfen (1 day residual) against *Puccinia recondita* on wheat.

The tank mix was obtained from technical material of Azolopyrimidine C and quinoxyfen. The observed and expected efficacies with different rates are given in Table XV:

TABLE XV

| dose rate (ppm) | | Observed | Expected |
|---|---|---|---|
| Azolopyrimidine C | quinoxyfen | Efficacy | Efficacy |
| 4 | 0 | 100 | — |
| 1 | 0 | 71 | — |
| 0.25 | 0 | 49 | — |
| 0.06 | 0 | 8 | — |
| 0 | 4 | 0 | — |
| 0 | 1 | 0 | — |
| 0 | 0.25 | 0 | — |
| 0 | 0.06 | 0 | — |
| 4 | 4 | 100 | 100 |
| 1 | 1 | 95 | 71 |
| 0.25 | 0.25 | 54 | 49 |
| 0.06 | 0.06 | 23 | 8 |

Example 16

Fungicidal efficacy of the mixture of Azolopyrimidine C+quinoxyfen (1 day residual)) against *Blumeria graminis* on wheat.

The tank mix was obtained from technical material of Azolopyrimidine C and quinoxyfen. The observed and expected efficacies with different rates are given in Table XVI:

TABLE XVI

| dose rate (ppm) | | Observed | Expected |
|---|---|---|---|
| Azolopyrimidine C | quinoxyfen | Efficacy | Efficacy |
| 4 | 0 | 96 | — |
| 1 | 0 | 42 | — |
| 0.25 | 0 | 19 | — |
| 0.06 | 0 | 0 | — |
| 0 | 4 | 99 | — |
| 0 | 1 | 73 | — |
| 0 | 0.25 | 18 | — |
| 0 | 0.06 | 8 | — |
| 4 | 4 | 100 | 100 |
| 1 | 1 | 87 | 85 |
| 0.25 | 0.25 | 53 | 33 |
| 0.06 | 0.06 | 24 | 8 |

Example 17

Fungicidal efficacy of the mixture of Azolopyrimidine C+metalaxyl (1 day residual) against *Blumeria graminis* on wheat.

The tank mix was obtained from technical material of Azolopyrimidine C and metalaxyl. The observed and expected efficacies with different rates are given in Table XVII:

TABLE XVII

| dose rate (ppm) | | Observed | Expected |
|---|---|---|---|
| Azolopyrimidine C | metalaxyl | Efficacy | Efficacy |
| 4 | 0 | 96 | — |
| 1 | 0 | 42 | — |
| 0.25 | 0 | 19 | — |
| 0.06 | 0 | 0 | — |
| 0 | 4 | 0 | — |
| 0 | 1 | 0 | — |
| 0 | 0.25 | 0 | — |
| 0 | 0.06 | 0 | — |
| 4 | 4 | 92 | 96 |
| 1 | 1 | 45 | 42 |
| 0.25 | 0.25 | 34 | 19 |
| 0.06 | 0.06 | 21 | 0 |

Example 18

Fungicidal efficacy of the mixture of Azolopyrimidine C+famoxadone (1 day residual) against *Blumeria graminis* on wheat.

The tank mix was obtained from technical material of Azolopyrimidine C and famoxadone. The observed and expected efficacies with different rates are given in Table XVIII:

TABLE XVIII

| dose rate (ppm) | | Observed | Expected |
|---|---|---|---|
| Azolopyrimidine C | Famoxadone | Efficacy | Efficacy |
| 4 | 0 | 96 | — |
| 1 | 0 | 42 | — |
| 0.25 | 0 | 19 | — |
| 0.06 | 0 | 0 | — |
| 0 | 4 | 0 | — |
| 0 | 1 | 0 | — |
| 0 | 0.25 | 0 | — |
| 0 | 0.06 | 0 | — |
| 4 | 4 | 96 | 96 |
| 1 | 1 | 53 | 42 |
| 0.25 | 0.25 | 34 | 19 |
| 0.06 | 0.06 | 9 | 0 |

Example 19

Fungicidal efficacy of the mixture of Azolopyrimidine C+famoxadone (1 day residual) against *Puccinia recondita* on wheat.

The tank mix was obtained from technical material of Azolopyrimidine C and famoxadone. The observed and expected efficacies with different rates are given in Table XIX:

TABLE XIX

| dose rate (ppm) | | Observed | Expected |
|---|---|---|---|
| Azolopyrimidine C | famoxadone | Efficacy | Efficacy |
| 4 | 0 | 100 | — |
| 1 | 0 | 71 | — |
| 0.25 | 0 | 49 | — |
| 0.06 | 0 | 8 | — |
| 0 | 4 | 61 | — |
| 0 | 1 | 31 | — |
| 0 | 0.25 | 0 | — |
| 0 | 0.06 | 0 | — |
| 4 | 4 | 100 | 100 |
| 1 | 1 | 87 | 80 |
| 0.25 | 0.25 | 52 | 49 |
| 0.06 | 0.06 | 29 | 8 |

Example 20

Fungicidal efficacy of the mixture of Azolopyrimidine C+dodine (1 day residual) against *Puccinia recondita* on wheat.

The tank mix was obtained from technical material of Azolopyrimidine C and a WP containing 650 g dodine per kg. The observed and expected efficacies with different rates are given in Table XX:

TABLE XX

| dose rate (ppm) | | Observed | Expected |
|---|---|---|---|
| Azolopyrimidine C | dodine | Efficacy | Efficacy |
| 0.86 | 0 | 8 | — |
| 0 | 0.06 | 0 | — |
| 0.06 | 0.06 | 28 | 8 |

Example 21

Fungicidal efficacy of the mixture of Azolopyrimidine C+copper oxychloride (1 day residual) against *Puccinia recondita* on wheat.

The tank mix was obtained from technical material of Azolopyrimidine C and a WP containing 450 g copper oxychloride per kg. The observed and expected efficacies with different rates are given in Table XXI:

TABLE XXI

| dose rate (ppm) | | Observed | Expected |
|---|---|---|---|
| Azolopyrimidine C | copper oxychloride | Efficacy | Efficacy |
| 0.06 | 0 | 8 | — |
| 0 | 0.06 | 0 | — |
| 0.06 | 0.06 | 18 | 8 |

Example 22

Fungicidal efficacy of the mixture of Azolopyrimidine C+sulfur (1 day residual) against *Puccinia recondita* on wheat.

The tank mix was obtained from technical material of Azolopyrimidine C and sulfur. The observed and expected efficacies with different rates are given in Table XXII:

TABLE XXII

| dose rate (ppm) | | Observed | Expected |
|---|---|---|---|
| Azolopyrimidine C | sulfur | Efficacy | Efficacy |
| 1 | 0 | 71 | — |
| 0 | 1 | 0 | — |
| 1 | 1 | 86 | 71 |

Example 23

Fungicidal efficacy of the mixture of Azolopyrimidine C+triforine (1 day residual) against *Erysiphe cichoracearum* on cucumbers.

The tank mix was obtained from a SC formulation containing 100 g of Azolopyrimidine C per liter and an DC formulation containing and 190 g of triforine per liter. The observed and expected efficacies with different rates are given in Table XXIII:

TABLE XXIII

| dose rate (ppm) | | Observed | Expected |
|---|---|---|---|
| Azolopyrimidine C | triforine | Efficacy | Efficacy |
| 4 | 0 | 7 | — |
| 1 | 0 | 0 | — |
| 0 | 16 | 15 | — |
| 0 | 4 | 0 | — |
| 4 | 16 | 47 | 34 |
| 1 | 4 | 12 | 0 |

Example 24

Fungicidal efficacy of the mixture of Azolopyrimidine C+cyprodinil (1 day residual) against *Erysiphe cichoracearum* on cucumbers.

The tank mix was obtained from a SC formulation containing 100 g of Azolopyrimidine C per liter and a WG formulation containing and 750 g of cyprodinil per kg. The observed and expected efficacies with different rates are given in Table XXIV:

TABLE XXIV

| dose rate (ppm) | | Observed | Expected |
|---|---|---|---|
| Azolopyrimidine C | cyprodinil | Efficacy | Efficacy |
| 4 | 0 | 7 | — |
| 1 | 0 | 0 | — |
| 0 | 16 | 29 | — |
| 0 | 4 | 0 | — |
| 4 | 16 | 41 | 34 |
| 1 | 4 | 10 | 0 |

Example 25

Fungicidal efficacy of the mixture of Azolopyrimidine C and different fungicides (1 day residual) against *Alternaria solani* on tomatoes.

The tank mix was obtained from an SC formulation containing 100 g Azolopyrimidine A per liter and WP formulations of dithianon (750 g/kg), captan (500 g/kg), cyprodinil (750 g/kg), mancozeb (800 g/kg), or a SC formulation of chlorothalonil (500 g/l), or a FS formulation of fenpiclonil (400 g/l), respectively. The observed and expected efficacies with different rates are given in Table XXV:

TABLE XXV

| Azolopyrimidine C (g/ha) | Cereal Fungicide | rate (g/ha) | Observed Efficacy | Expected Efficacy |
|---|---|---|---|---|
| 4 | — | 0 | 25 | — |
| 0 | dithianon | 16 | 50 | — |
| 0 | captan | 16 | 18 | — |
| 0 | cyprodinil | 16 | 13 | — |
| 0 | mancozeb | 16 | 27 | — |
| 0 | chlorothalonil | 16 | 13 | — |
| 0 | fenpiclonil | 16 | 76 | — |
| 4 | dithianon | 16 | 76 | 63 |
| 4 | captan | 16 | 60 | 38 |
| 4 | cyprodinil | 16 | 50 | 35 |
| 4 | mancozeb | 16 | 62 | 45 |
| 4 | chlorothalonil | 16 | 57 | 35 |
| 4 | fenpiclonil | 16 | 91 | 82 |

Example 26

Fungicidal efficacy of the mixture of (S)-Azolopyrimidine C in admixture with Fenhexamid (2 days curative) against *Blumeria graminis* on barley.

The tank mixes were obtained from technical material of (S)-Azolopyrimidine C and Fenhexamid. The active ingredients, the observed and expected efficacies with different rates are given in Table XXVI:

TABLE XXVI

| Compound | dose rate (ppm) | Observed Efficacy | Expected Efficacy |
|---|---|---|---|
| (S)-Azolopyrimidine C | 180 | 86 | |
| | 60 | 60 | |
| | 20 | 37 | |
| | 6.7 | 29 | |
| | 2.2 | 8 | |
| | 0.74 | 0 | |
| Fenhexamid | 180 | 39 | |
| | 60 | 7 | |
| | 20 | 1 | |
| | 6.7 | 0 | |
| | 2.2 | 0 | |
| | 0.74 | 0 | |
| (S)-Azolopyrimidine C + Fenhexamid | 180 + 180 | 95 | 91 |
| | 60 + 60 | 70 | 63 |
| | 20 + 20 | 42 | 38 |
| | 6.7 + 6.7 | 36 | 29 |
| | 2.2 + 2.2 | 18 | 8 |
| | 0.74 + 0.74 | 8 | 0 |

Example 27

Fungicidal efficacy of the mixture of (S)-Azolopyrimidine C in admixture with Azoxystrobin or Trifloxystrobin (2 days curative) against *Blumeria graminis* on wheat.

The tank mixes were obtained from technical material of (S)-Azolopyrimidine C and Azoxystrobin or Trifloxystrobin. The active ingredients, the observed and expected efficacies with different rates are given in Table XXVII:

TABLE XXVII

| Compound | dose rate (ppm) | Observed Efficacy | Expected Efficacy |
|---|---|---|---|
| (S)-Azolopyrimidine C | 50 | 81 | |
| | 25 | 61 | |
| | 12.5 | 40 | |
| | 6.3 | 10 | |
| | 3.1 | 0 | |
| | 1.6 | 0 | |
| Azoxystrobin | 50 | 61 | |
| | 25 | 48 | |
| | 12.5 | 28 | |
| | 6.3 | 21 | |
| | 3.1 | 2 | |
| | 1.6 | 0 | |
| Trifloxystrobin | 50 | 99 | |
| | 25 | 98 | |
| | 12.5 | 89 | |
| | 6.3 | 78 | |
| | 3.1 | 55 | |
| | 1.6 | 34 | |
| (S)-Azolopyrimidine C + Azoxystrobin | 50 + 50 | 95 | 93 |
| | 25 + 25 | 79 | 80 |
| | 12.5 + 12.5 | 62 | 57 |
| | 6.3 + 6.3 | 30 | 29 |
| | 3.1 + 3.1 | 20 | 2 |
| | 1.6 + 1.6 | 14 | 0 |
| (S)-Azolopyrimidine C + Trifloxystrobin | 50 + 50 | 100 | 100 |
| | 25 + 25 | 100 | 99 |
| | 12.5 + 12.5 | 93 | 93 |
| | 6.3 + 6.3 | 75 | 80 |
| | 3.1 + 3.1 | 67 | 55 |
| | 1.6 + 1.6 | 45 | 34 |

Example 28

Fungicidal efficacy of the mixture of (S)-Azolopyrimidine C in admixture with Azoxystrobin or Trifloxystrobin (2 days curative) against *Puccinia recondita* on wheat.

The tank mixes were obtained from technical material of (S)-Azolopyrimidine C and Azoxystrobin or Trifloxystrobin. The active ingredients, the observed and expected efficacies with different rates are given in Table XXVIII:

TABLE XXVIII

| Compound | dose rate (ppm) | Observed Efficacy | Expected Efficacy |
|---|---|---|---|
| S)-Azolopyrimidine C | 25 | 54 | |
| | 12.5 | 23 | |
| | 6.3 | 8 | |
| | 3.1 | 0 | |
| | 1.6 | 0 | |
| Azoxystrobin | 25 | 95 | |
| | 12.5 | 85 | |
| | 6.3 | 48 | |
| | 3.1 | 25 | |
| | 1.6 | 0 | |
| Trifloxystrobin | 25 | 0 | |
| | 12.5 | 0 | |
| | 6.3 | 0 | |
| | 3.1 | 0 | |
| | 1.6 | 0 | |
| (S)-Azolopyrimidine C + Azoxystrobin | 25 + 25 | 99 | 98 |
| | 12.5 + 12.5 | 87 | 88 |
| | 6.3 + 6.3 | 81 | 52 |
| | 3.1 + 3.1 | 45 | 25 |
| | 1.6 + 1.6 | 18 | 0 |
| (S)-Azolopyrimidine C + Trifloxystrobin | 25 + 25 | 53 | 54 |
| | 12.5 + 12.5 | 36 | 23 |
| | 6.3 + 6.3 | 15 | 8 |
| | 3.1 + 3.1 | 5 | 0 |
| | 1.6 + 1.6 | 0 | 0 |

Example 29

Fungicidal efficacy of the mixture of (S)-Azolopyrimidine C in admixture with Azoxystrobin or Trifloxystrobin (2 days curative) against *Blumeria graminis* on barley.

The tank mixes were obtained from technical material of (S)-Azolopyrimidine C and Azoxystrobin or Trifloxystrobin. The active ingredients, the observed and expected efficacies with different rates are given in Table XXIX:

TABLE XXIX

| Compound | dose rate (ppm) | Observed Efficacy | Expected Efficacy |
|---|---|---|---|
| (S)-Azolopyrimidine C | 50 | 73 | |
| | 25 | 54 | |
| | 12.5 | 31 | |
| | 6.3 | 15 | |
| | 3.1 | 1 | |
| | 1.6 | 0 | |
| Azoxystrobin | 50 | 87 | |
| | 25 | 73 | |
| | 12.5 | 49 | |
| | 6.3 | 21 | |
| | 3.1 | 10 | |
| | 1.6 | 0 | |
| Trifloxystrobin | 50 | 96 | |
| | 25 | 89 | |
| | 12.5 | 74 | |
| | 6.3 | 59 | |
| | 3.1 | 36 | |
| | 1.6 | 22 | |
| (S)-Azolopyrimidine C + Azoxystrobin | 50 + 50 | 98 | 96 |
| | 25 + 25 | 90 | 88 |
| | 12.5 + 12.5 | 75 | 65 |
| | 6.3 + 6.3 | 51 | 33 |
| | 3.1 + 3.1 | 18 | 11 |
| | 1.6 + 1.6 | 1 | 1 |
| (S)-Azotopyrimidine C + Trifloxystrobin | 50 + 50 | 100 | 99 |
| | 25 + 25 | 98 | 95 |
| | 12.5 + 12.5 | 87 | 82 |
| | 6.3 + 6.3 | 61 | 65 |
| | 3.1 + 3.1 | 46 | 37 |
| | 1.6 + 1.6 | 28 | 22 |

Example 30

Fungicidal efficacy of the mixture of (S)-Azolopyrimidine C in admixture with Azoxystrobin or Trifloxystrobin (4 days residual) against *Blumeria graminis* on wheat.

The tank mixes were obtained from technical material of (S)-Azolopyrimidine C and Azoxystrobin or Trifloxystrobin. The active ingredients, the observed and expected efficacies with different rates are given in Table XXX:

TABLE XXX

| Compound | dose rate (ppm) | Observed Efficacy | Expected Efficacy |
| --- | --- | --- | --- |
| (S)-Azolopyrimidine C | 50 | 34 | |
| | 25 | 11 | |
| | 12.5 | 3 | |
| | 6.3 | 0 | |
| | 3.1 | 0 | |
| Azoxystrobin | 50 | 9 | |
| | 25 | 9 | |
| | 12.5 | 7 | |
| | 6.3 | 0 | |
| | 3.1 | 0 | |
| Trifloxystrobin | 50 | 14 | |
| | 25 | 0 | |
| | 12.5 | 0 | |
| | 6.3 | 0 | |
| | 3.1 | 0 | |
| (S)-Azolopyrimidine C + Azoxystrobin | 50 + 50 | 49 | 40 |
| | 25 + 25 | 25 | 19 |
| | 12.5 + 12.5 | 18 | 10 |
| | 6.3 + 6.3 | 1 | 0 |
| | 3.1 + 3.1 | 0 | 0 |
| (S)-Azolopyrimidine C + Trifloxystrobin | 50 + 50 | 51 | 43 |
| | 25 + 25 | 27 | 11 |
| | 12.5 + 12.5 | 29 | 3 |
| | 6.3 + 6.3 | 7 | 0 |
| | 3.1 + 3.1 | 9 | 0 |

Example 31

Fungicidal efficacy of the mixture of (S)-Azolopyrimidine C in admixture with Azoxystrobin or Trifloxystrobin (4 days residual) against *Puccinia recondita* on wheat.

The tank mixes were obtained from technical material of (S)-Azolopyrimidine C and Azoxystrobin or Trifloxystrobin. The active ingredients, the observed and expected efficacies with different rates are given in Table XXXI:

TABLE XXXI

| Compound | dose rate (ppm) | Observed Efficacy | Expected Efficacy |
| --- | --- | --- | --- |
| (S)-Azolopyrimidine C | 50 | 50 | |
| | 25 | 27 | |
| | 12.5 | 16 | |
| | 6.3 | 9 | |
| | 3.1 | 0 | |
| Azoxystrobin | 50 | 8 | |
| | 25 | 0 | |
| | 12.5 | 0 | |
| | 6.3 | 0 | |
| | 3.1 | 0 | |
| Trifloxystrobin | 50 | 0 | |
| | 25 | 0 | |
| | 12.5 | 0 | |
| | 6.3 | 0 | |
| | 3.1 | 0 | |
| (S)-Azolopyrimidine C + Azoxystrobin | 50 + 50 | 63 | 54 |
| | 25 + 25 | 28 | 27 |
| | 12.5 + 12.5 | 21 | 16 |
| | 6.3 + 6.3 | 10 | 9 |
| | 3.1 + 3.1 | 6 | 0 |
| (S)-Azolopyrimidine C + Trifloxystrobin | 50 + 50 | 59 | 50 |
| | 25 + 25 | 35 | 27 |
| | 12.5 + 12.5 | 15 | 16 |
| | 6.3 + 6.3 | 10 | 9 |
| | 3.1 + 3.1 | 1 | 0 |

Example 32

Fungicidal efficacy of the mixture of (S)-Azolopyrimidine C in admixture with Azoxystrobin (4 days residual) against *Blumeria graminis* on barley.

The tank mixes were obtained from technical material of (S)-Azolopyrimidine C and Azoxystrobin. The active ingredients, the observed and expected efficacies with different rates are given in Table XXXII:

TABLE XXXII

| Compound | dose rate (ppm) | Observed Efficacy | Expected Efficacy |
| --- | --- | --- | --- |
| (S)-Azolopyrimidine C | 50 | 28 | |
| | 25 | 22 | |
| | 12.5 | 17 | |
| | 6.3 | 8 | |
| | 3.1 | 3 | |
| | 1.6 | 0 | |
| Azoxystrobin | 50 | 9 | |
| | 25 | 2 | |
| | 12.5 | 3 | |
| | 6.3 | 3 | |
| | 3.1 | 3 | |
| | 1.6 | 0 | |
| (S)-Azolopyrimidine C + Azoxystrobin | 50 + 50 | 39 | 34 |
| | 25 + 25 | 34 | 24 |
| | 12.5 + 12.5 | 27 | 19 |
| | 6.3 + 6.3 | 20 | 11 |
| | 3.1 + 3.1 | 20 | 6 |
| | 1.6 + 1.6 | 14 | 0 |

B Field Tests

Example 33

Fungicidal efficacy of the mixture of Azolopyrimidine B+pyrimethanil in the field against *Botrytis cinerea* in vines The tank mix was obtained from a SC formulation containing 100 g of Azolopyrimidine B per liter and a SC formulation containing 400 g of pyrimethanil per liter. The observed and expected efficacies are given in Table XXXIII:

TABLE XXXIII

| dose rate (g/ha) | | Observed | Expected |
| --- | --- | --- | --- |
| Azolopyrimidine B | pyrimethanil | Efficacy | Efficacy |
| 250 | 0 | 58 | — |
| 0 | 500 | 66 | — |
| 250 | 500 | 92 | 86 |

Example 34

Fungicidal efficacy of the mixture of Azolopyrimidine C+metconazole in the field against *Septoria tritici* on wheat.

The tank mix was obtained from an EC formulation containing 150 g Azolopyrimidine C per liter and a SL formulation containing 60 g metconazole per liter. The observed and expected efficacies with different rates are given in Table XXXIVa (19 days after application) and Table XXXIVb (25 days after application):

TABLE XXXIVa

| dose rate (g/ha) | | Observed | Expected |
| --- | --- | --- | --- |
| Azolopyrimidine C | Metconazole | Efficacy | Efficacy |
| 25 | 0 | 48 | — |
| 0 | 15 | 9 | — |

TABLE XXXIVa-continued

| dose rate (g/ha) | | Observed | Expected |
|---|---|---|---|
| Azolopyrimidine C | Metconazole | Efficacy | Efficacy |
| 0 | 30 | 36 | — |
| 0 | 45 | 24 | — |
| 25 | 15 | 73 | 53 |
| 25 | 30 | 74 | 67 |
| 25 | 45 | 76 | 60 |

TABLE XXXIVb

| dose rate (g/ha) | | Observed | Expected |
|---|---|---|---|
| Azolopyrimidine C | Metconazole | Efficacy | Efficacy |
| 50 | 0 | 61 | — |
| 75 | 0 | 13 | — |
| 0 | 15 | 33 | — |
| 0 | 60 | 48 | — |
| 50 | 15 | 82 | 74 |
| 75 | 60 | 66 | 55 |

Example 35

Fungicidal efficacy of the mixture of (S)-Azolopyrimidine C+kresoxim methyl in the field against *Septoria tritici* on wheat.

The tank mix was obtained from a SC formulation containing 100 g (S)-Azolopyrimidine C per liter and a WG formulation containing 500 g kresoxim methyl per kg. The observed and expected efficacies with different rates are given in Tables XXXVa (7 days after application), XXXVb (22 days after application), XXXVc (34 days after application), and XXXVd (41 days after application):

TABLE XXXVa

| dose rate (g/ha) | | Observed | Expected |
|---|---|---|---|
| (S)-Azolopyrimidine C | kresoxim methyl | Efficacy | Efficacy |
| 25 | 0 | 34 | — |
| 0 | 100 | 40 | — |
| 25 | 100 | 70 | 60 |

TABLE XXXVb

| dose rate (g/ha) | | Observed | Expected |
|---|---|---|---|
| (S)-Azolopyrimidine C | kresoxim methyl | Efficacy | Efficacy |
| 25 | 0 | 74 | — |
| 100 | 0 | 87 | — |
| 0 | 100 | 64 | — |
| 25 | 100 | 92 | 87 |
| 100 | 100 | 99 | 96 |

TABLE XXXVc

| dose rate (g/ha) | | Observed | Expected |
|---|---|---|---|
| (S)-Azolopyrimidine C | kresoxim methyl | Efficacy | Efficacy |
| 50 | 0 | 53 | — |
| 100 | 0 | 70 | — |
| 0 | 50 | 44 | — |

TABLE XXXVc-continued

| dose rate (g/ha) | | Observed | Expected |
|---|---|---|---|
| (S)-Azolopyrimidine C | kresoxim methyl | Efficacy | Efficacy |
| 0 | 100 | 59 | — |
| 50 | 100 | 88 | 83 |
| 100 | 50 | 84 | 83 |
| 100 | 100 | 92 | 88 |

TABLE XXXVd

| dose rate (g/ha) | | Observed | Expected |
|---|---|---|---|
| (S)-Azolopyrimidine C | kresoxim methyl | Efficacy | Efficacy |
| 75 | 0 | 92 | — |
| 0 | 100 | 92 | — |
| 75 | 100 | 100 | 98 |

Example 36

Fungicidal efficacy of the mixture of (S)-Azolopyrimidine C+cyproconazole in the field against *Blumeria graminis* on wheat 17 days after application.

The tank mix was obtained from a SC formulation containing 100 g (S)-Azolopyrimidine C per liter and an EC formulation containing 60 g cyproconazole per liter. The observed and expected efficacies with different rates are given in Table XXXVI:

TABLE XXXVI

| dose rate (g/ha) | | Observed | Expected |
|---|---|---|---|
| (S)-Azolopyrimidine C | cyproconazole | Efficacy | Efficacy |
| 25 | 0 | 63 | — |
| 50 | 0 | 78 | — |
| 75 | 0 | 74 | — |
| 0 | 15 | 86 | — |
| 0 | 30 | 82 | — |
| 25 | 15 | 96 | 95 |
| 25 | 30 | 98 | 93 |
| 50 | 30 | 100 | 96 |
| 75 | 30 | 98 | 95 |

Example 37

Fungicidal efficacy of the mixture of (S)-Azolopyrimidine C+azoxystrobin in the field against *Blumeria graminis* on wheat 17 days after application.

The tank mix was obtained from a SC formulation containing 100 g (S)-Azolopyrimidine C per liter and a SC formulation containing 250 g azoxystrobin per kg. The observed and expected efficacies with different rates are given in Table XXXVII:

TABLE XXXVII

| dose rate (g/ha) | | Observed | Expected |
|---|---|---|---|
| (S)-Azolopyrimidine C | Azoxystrobin | Efficacy | Efficacy |
| 25 | 0 | 63 | — |
| 50 | 0 | 78 | — |
| 75 | 0 | 74 | — |
| 100 | 0 | 96 | — |

TABLE XXXVII-continued

| dose rate (g/ha) | | Observed Efficacy | Expected Efficacy |
|---|---|---|---|
| (S)-Azolopyrimidine C | Azoxystrobin | | |
| 0 | 75 | 49 | — |
| 25 | 75 | 92 | 81 |
| 50 | 75 | 94 | 89 |
| 75 | 75 | 92 | 86 |
| 100 | 75 | 100 | 98 |

Example 38

Fungicidal efficacy of the mixture of Azolopyrimidine A and different cereal fungicides in the field against *Blumeria graminis* on wheat 15 days after application.

The tank mix was obtained from an SC formulation containing 100 g Azolopyrimidine A per liter and commercially available formulations of metconazole, epoxiconazole or kresoxim methyl, respectively. The observed and expected efficacies with different rates are given in Table XXXVIII:

TABLE XXXVIII

| Azolopyrimidine A | Cereal Fungicide | rate (g/ha) | Observed Efficacy | Expected Efficacy |
|---|---|---|---|---|
| 125 | — | 0 | 22 | — |
| 0 | metconazole | 45 | 54 | — |
| 0 | epoxiconazole | 63 | 40 | — |
| 0 | kresoxim methyl | 100 | 85 | — |
| 125 | metconazole | 45 | 79 | 64 |
| 125 | epoxiconazole | 63 | 74 | 53 |
| 125 | kresoxim methyl | 100 | 92 | 88 |

Example 39

Fungicidal efficacy of the mixture of Azolopyrimidine A and different cereal fungicides the field against *Septoria tritici* on wheat 15 days after application.

The tank mix was obtained from an SC formulation containing 100 g Azolopyrimidine A per liter and commercially available formulations of metconazole, epoxiconazole or propiconazole, respectively. The observed and expected efficacies with different rates are given in Table XXXIX:

TABLE XXXIX

| Azolopyrimidine A | Cereal Fungicide | rate (g/ha) | Observed Efficacy | Expected Efficacy |
|---|---|---|---|---|
| 125 | — | 0 | 63 | — |
| 0 | metconazole | 45 | 77 | — |
| 0 | epoxiconazole | 63 | 93 | — |
| 0 | propiconazole | 63 | 72 | — |
| 125 | metconazole | 45 | 99 | 91 |
| 125 | epoxiconazole | 63 | 97 | 97 |
| 125 | propiconazole | 63 | 93 | 90 |

Example 40

Fungicidal efficacy of the mixture of Azolopyrimidine A and different cereal fungicides in the field against *Puccinia recondita* on wheat 50 days after application.

The tank mix was obtained from an SC formulation containing 100 g Azolopyrimidine A per liter and commercially available formulations of metconazole, epoxiconazole, propiconazole or kresoxim methyl, respectively. The observed and expected efficacies with different rates are given in Table XXXX:

TABLE XXXX

| Azolopyrimidine A | Cereal Fungicide | rate (g/ha) | Observed Efficacy | Expected Efficacy |
|---|---|---|---|---|
| 125 | — | 0 | 0 | — |
| 0 | metconazole | 45 | 75 | — |
| 0 | epoxiconazole | 63 | 95 | — |
| 0 | propiconazole | 63 | 49 | — |
| 0 | kresoxim methyl | 100 | 0 | — |
| 125 | metconazole | 45 | 85 | 75 |
| 125 | epoxiconazole | 63 | 97 | 95 |
| 125 | propiconazole | 63 | 67 | 49 |
| 125 | kresoxim methyl | 100 | 64 | 0 |

What is claimed is:

1. A fungicidal composition comprising a fungicidally acceptable carrier and/or surface active agent and synergistically effective amounts of
   (a) at least one azolopyrimidine of formula I

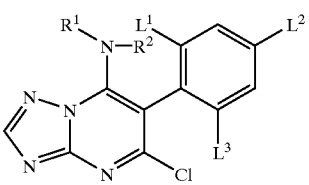

(I)

in which
$R^1$ represents a $C_{1-6}$ alkyl, $C_{3-6}$ alkenyl or $C_{1-6}$ haloalkyl group, and
$R^2$ represents a hydrogen atom or a $C_{1-6}$ alkyl group, or
$R^1$ and $R^2$ taken together represent a $C_{3-8}$ alkylene group;
$L^1$ represents a halogen atom; and
$L^2$ and $L^3$ each independently represent a hydrogen or a halogen atom; and
   (b) at least one fungicidal active ingredient selected from the group consisting of benomyl, carboxin, captan, chlorothalonil, copper oxychloride, cyprodinil, dimethomorph, dithianon, dodine, famoxadone, fenhexamid, fenpiclonil, fenpropimorph, fluazinam, mancozeb, metalaxyl, pyrimethanil, quinoxifen, sulfur, triforine and vinclozolin.

2. A composition as claimed in claim 1 wherein in the compound of formula I

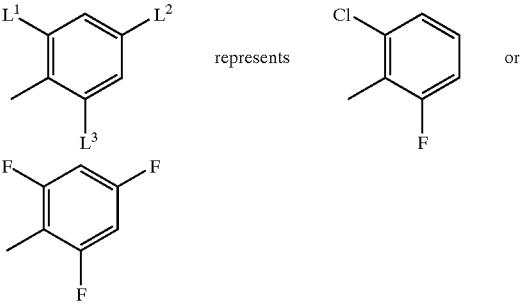

3. A composition as claimed in claim 2, wherein the azolopyrimidine is selected from the group consisting of: 5-chloro-6-(2-chloro-6-fluorophenyl)-7-(4-methylpiperid-1-yl)[1,2,4]triazolo[1,5-a]pyrimidine, 5-chloro-6-(2-chloro-6-fluorophenyl)-7-(2,2,2-trifluoroethylamino) [1,2,4]triazolo[1,5-a]pyrimidine, and 5-chloro-6-(2,4,6-trifluorophenyl) 7-(1,1,1-trifluoroprop-2-ylamino) [1,2,4]triazolo[1,5-a]pyrimidine.

4. A composition as claimed in claim 1, wherein the ratio (by weight) of the fungicidal compound (b) to the azolopyrimidine of formula I (a) is approximately from 0.01:1 to 100:1.

5. A method of controlling the growth of phytopathogenic fungi at a locus which comprises applying an effective amount of the composition defined in claim 1 to the locus.

6. The method of claim 5 wherein the phytopathogenic fungi are wheat leaf rust, wheat Septoria leaf blotch or wheat powdery mildew.

7. The composition defined in claim 1 wherein at least one fungicidal active ingredient is selected from the group consisting of benomyl, carboxin, captan, chlorothalonil, copper oxychloride, cyprodinil, dimethomorph, dithianon, dodine, famoxadone, fenpiclonil, fenpropimorph, fluazinam, mancozeb, metalaxyl, pyrimethanil, quinoxifen, sulfur, triforine and vinclozolin.

8. A composition as claimed in claim 7 wherein in the compound of formula I

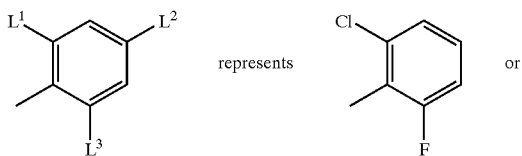 represents 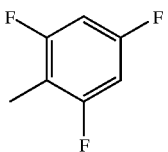 or

9. A composition as claimed in claim 8, wherein the azolopyrimidine is selected from the group consisting of: 5-chloro-6-(2-chloro-6-fluorophenyl)-7-(4-methylpiperid-1-yl)[1,2,4]triazolo[1,5-a]pyrimidine, 5-chloro-6-(2-chloro-6-fluorophenyl)-7-(2,2,2-trifluoroethylamino) [1,2,4] triazolo[1,5-a]pyrimidine, and 5-chloro-6-(2,4,6-trifluorophenyl)-7-(1,1,1-trifluoroprop-2-ylamino) [1,2,4] triazolo[1,5-a]pyrimidine.

10. A composition as claimed in claim 7, wherein the ratio (by weight) of the fungicidal compound (b) to the azolopyrimidine of formula I (a) is approximately from 0.01:1 to 100:1.

11. A method of controlling the growth of phytopathogenic fungi at a locus which comprises applying an effective amount of the composition defined in claim 7 to the locus.

* * * * *